United States Patent [19]

Joshi

[11] Patent Number: 5,765,751
[45] Date of Patent: Jun. 16, 1998

[54] CONTROLLED RELEASE OF VOLATILE SUBSTANCES

[75] Inventor: Ashok V. Joshi, Salt Lake City, Utah

[73] Assignee: Ceramatec, Inc., Salt Lake City, Utah

[21] Appl. No.: 686,730

[22] Filed: Jul. 26, 1996

[51] Int. Cl.$^6$ ............................................. A61L 9/04
[52] U.S. Cl. ............................................. 239/56
[58] Field of Search ......................... 239/53–57, 36, 239/60

[56] References Cited

U.S. PATENT DOCUMENTS

| | | | |
|---|---|---|---|
| 2,564,860 | 8/1951 | Ryberg | 239/55 X |
| 2,615,754 | 10/1952 | Lindenberg | 239/56 X |
| 2,740,662 | 4/1956 | Scott | 239/55 |
| 3,685,734 | 8/1972 | Paciorek et al. | |
| 4,081,501 | 3/1978 | Muther | |
| 4,145,001 | 3/1979 | Weyenberg et al. | |
| 4,157,787 | 6/1979 | Schwartz | 239/60 X |
| 4,254,910 | 3/1981 | Martin | |
| 4,292,383 | 9/1981 | Di Palma et al. | 429/219 |
| 4,753,389 | 6/1988 | Davis | 239/56 X |
| 4,849,606 | 7/1989 | Martens, III et al. | |
| 5,007,529 | 4/1991 | Spector | |
| 5,230,867 | 7/1993 | Kunze et al. | 239/57 X |
| 5,242,111 | 9/1993 | Nakoneczny et al. | |
| 5,266,543 | 11/1993 | Matsumoto et al. | |
| 5,291,742 | 3/1994 | Kawatani et al. | |
| 5,361,522 | 11/1994 | Green | |
| 5,372,303 | 12/1994 | Paul | |
| 5,373,581 | 12/1994 | Smith | |
| 5,399,404 | 3/1995 | Laughlin et al. | |
| 5,431,859 | 7/1995 | Tobin | |
| 5,437,410 | 8/1995 | Babasade | |
| 5,439,100 | 8/1995 | Gordon et al. | |
| 5,447,693 | 9/1995 | Ohta et al. | |
| 5,468,447 | 11/1995 | Bermas | |
| 5,478,505 | 12/1995 | McElfresh et al. | |
| 5,487,869 | 1/1996 | Retallick | |

OTHER PUBLICATIONS

Eury et al., Abstract, "Blocked polymeric particles having internal pore networks for delivering active substances to selected environments", U.S. Patent No. 5,316,774, May 31, 1994, 2 pages.

Williford et al., Abstract, "Methods and compositions for flavoring orally-delivered products", U.S. Patent No. 5,458,890, Oct. 17, 1995, 2 pages.

*Primary Examiner*—Andres Kashnikow
*Assistant Examiner*—Steven J. Ganey
*Attorney, Agent, or Firm*—Dick and Harris

[57] ABSTRACT

A "button cell" battery-type volatile substance delivery device includes a thin-walled metallic canister (11) with apertures (14) at the closed end thereof which allows volatile fluid to escape therefrom as a vapor. A permeable membrane (13) such as a microporous membrane is positioned in one end of the canister and is sealed with a cap (16) and grommet (12) assembly. Volatile fluid is placed in the cap and grommet assembly prior to placement of the canister for crimping of the device to form a hermetic seal between the canister and the cap as well as a hermetic seal between the canister and permeable membrane along the perimeter of the closed end of the canister. These two seals allow volatile fluid contained in the cell to diffuse only through the permeable membrane at a controlled rate. The rate of evaporation of the fluid depends on the characteristics of the membrane and the number of apertures. Tape may be placed over the apertures to prevent volatilization of fluid until it is ready to be used. The volatile substance delivery devices are rugged and may be mass-manufactured at low cost. Volatile substances which can be dispensed include fragrances, personal perfumes, volatile insecticides, pest repellent fluids, and volatile medicament fluid compounds.

16 Claims, 3 Drawing Sheets

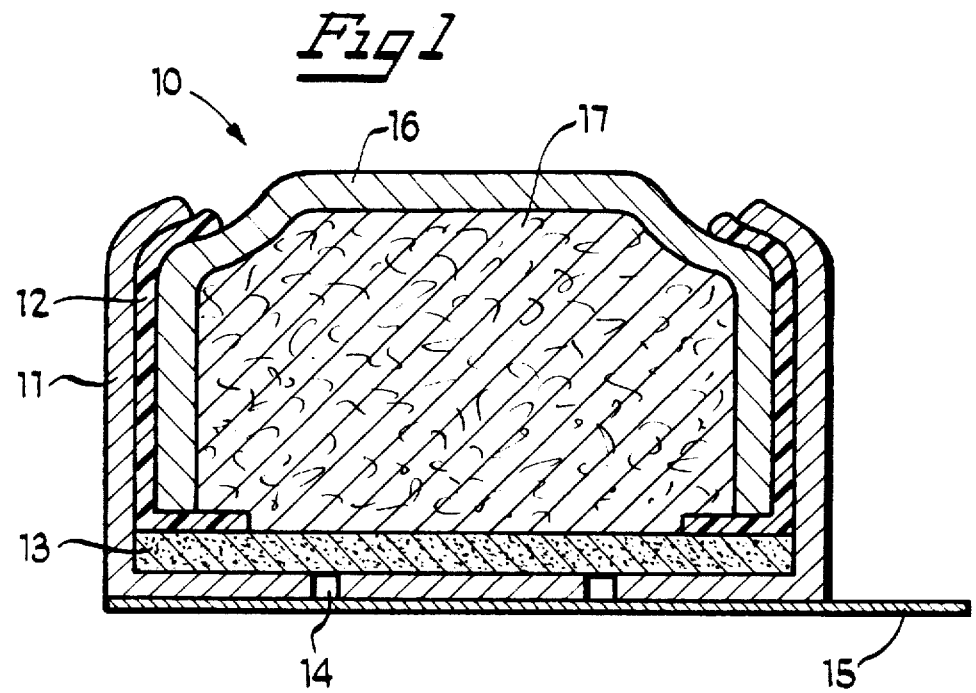
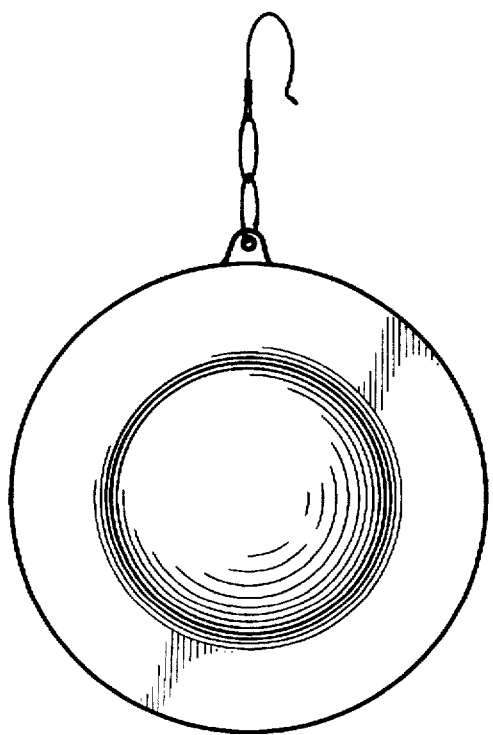
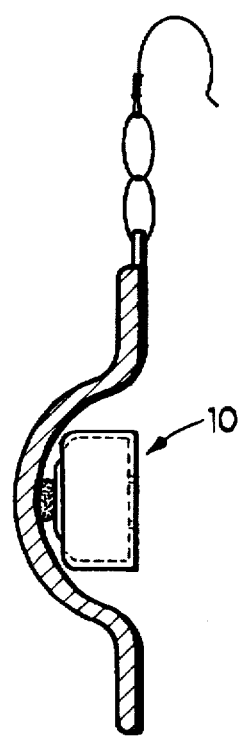

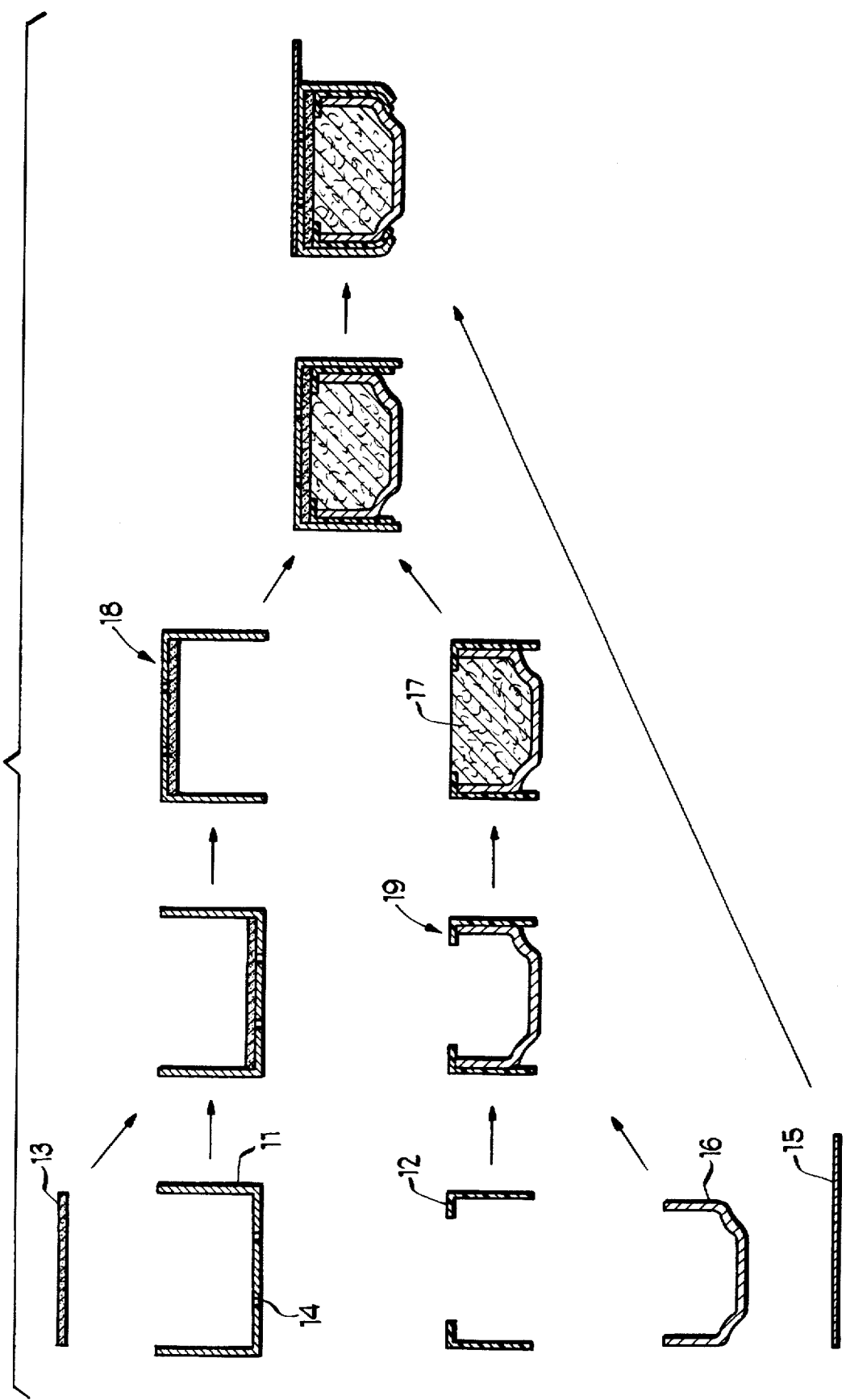

CONTROLLED RELEASE OF VOLATILE SUBSTANCES

TECHNICAL FIELD

This invention generally relates to devices and associated methods useful in the release of volatile substances. More specifically, the invention relates to a device useful in the controlled and prolonged release of volatile liquid compounds such as perfumes, fragrances, pesticides, pest repellents, and other volatile substances.

BACKGROUND

Patents exist describing devices for dispensing volatile substances in the air through a diffusion phenomenon. For instance, U.S. Pat. No. 3,685,734 to Paciorek et al. (Aug. 22, 1972) describes a multi-layer polymeric controlled fragrance-release device. The Paciorek et al. device uses a separate flexible sheet to cover a fragrance bearing middle sheet of plastisol. This cover sheet has very low vapor transmission, but upon its removal, fragrance is immediately detectable and is gradually released from the device.

U.S. Pat. No. 4,145,001 to Weyenberg et al. (Mar. 20, 1979) also describes a multi-layer polymeric package for the controlled release of a volatile substance (e.g. deodorizer) sandwiched between layers. The outer layers of the laminate are impermeable to the volatile substance and its vapors and thus prevent escape of vapors as long as the package is sealed. Upon opening the package, delamination occurs at the interface between two selected layers such that the volatile substance is covered only on one side by a layer which is permeable to vapors thereby allowing controlled release of volatile materials.

U.S. Pat. No. 5,242,111 to Nakoneczny et al. (Sep. 7, 1993) describes a liquid dispensing device which consists of a sealed flexible bag or pouch containing the supply of the active volatile fluid, a wick located inside a tubular chamber and an emanator which diffuses the liquid. U.S. Pat. No. 5,437,410 to Babasade (Aug. 1, 1995) also describes the use of a wick to dispense a fragrance.

U.S. Pat. No. 4,849,606 to Martens, III et al. (Jul. 18, 1989) describes a tamper-resistant plastic container which has a multi-layered flexible seal over its open end. The container has at least one free standing grid which prevents downward pressure or squeezing of the container's seal which might rupture the seal or result in a leakage of the fluid.

U.S. Pat. No. 5,478,505 to McElfresh et al. (Dec. 26, 1995) describes a device for dispensing air fragrance into the atmosphere. This device has an attachment clip and uses low density polyethylene as a diffusion membrane. This membrane is sealed to a plastic container similarly to U.S. Pat. No. 4,849,606 to Martens, III et al.

The prior art is not believed to disclose miniature devices using a rugged metallic housing in conjunction with rugged seals as is disclosed herein.

DISCLOSURE OF THE INVENTION

The invention includes a "button cell" battery-type device having a thin-walled metallic canister with apertures at the closed end thereof which apertures allow volatile fluid to escape therethrough as a vapor. A permeable membrane (such as a microporous membrane) is positioned in one end of the canister and is sealed with a metallic cap and plastic grommet assembly. Volatile fluid is placed in the cap-grommet assembly prior to placement of the canister with placed permeable membrane over the cap-grommet assembly for hermetic crimping of the device to form a hermetic seal between the canister and the cap as well as a hermetic seal between the canister and permeable membrane along the perimeter of closed end of the canister. These two hermetic seals allow volatile fluid contained in the cell to diffuse only through the permeable membrane at a controlled rate. The rate of evaporation of the fluid inside the envelope depends on the characteristics of the membrane and the number of apertures. Material such as non-porous, non-permeable polymeric or metallic adhesive tape may be placed on the apertures to prevent volatilization of fluid until it is ready to be actuated.

The volatile substance delivery devices of the instant invention are rugged and may be mass-produced at a relatively low cost. Volatile substances which can be dispensed include fragrances, personal perfumes, volatile insecticides, pesticides, pest repellent fluids, and volatile medicaments.

BRIEF DESCRIPTION OF THE FIGURES

In the drawings, which depict presently preferred embodiments of the invention and in which like reference numerals refer to like parts in different views:

FIG. 1 depicts an enlarged, somewhat stylized, cross-section of a button cell device according to the invention in an inactivated state.

FIG. 2 depicts a process of assembling the button cell device according to the invention from various components.

FIG. 5 is a front view of a button cell perfume-emanating device incorporated into an earring.

FIG. 6 is a partially cut-away, side view of the device of the preceding figure.

BEST MODE OF THE INVENTION

Figure 3:
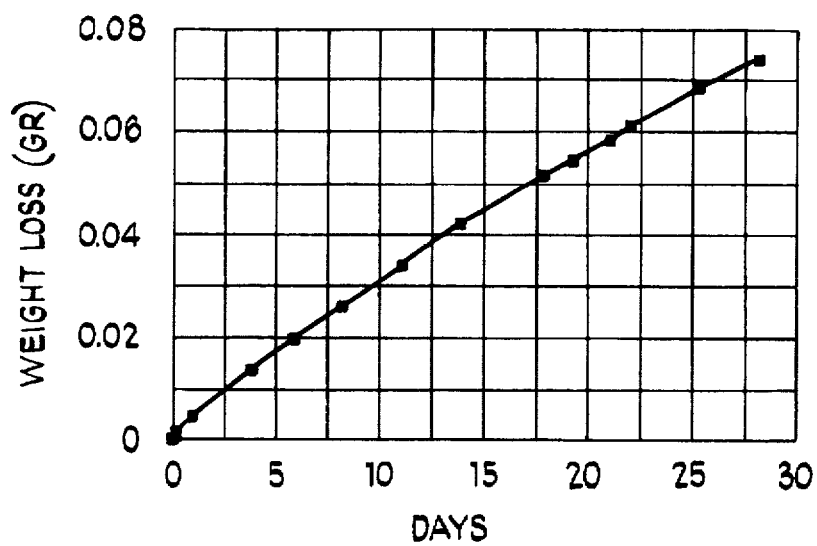
FIG. 3 is a graph depicting weight loss in mass (grams) versus time (days) from a fragrance-releasing button cell device according to the invention, showing controlled linear release of fragrance from the device.

For the purposes of illustration of the present invention, an embodiment of the controlled release of volatile substances device is shown in FIG. 1. The device, generally 10, shown is circular in cross-section which improves ease of fabrication; however, other shapes such as a square, rectangle, triangle or other shape are also possible and may be desired for aesthetic reasons or to facilitate incorporation into other structures such as jewelry as shown in FIGS. 5 and 6.

Referring to the cross-sectional view of the device shown in FIG. 1, the outer canister 11 may generally be constructed out of metal by a deep drawing method. The pure metal or metal alloy is chosen so that it is relatively inert with the volatile substance contained within the device. For example, for most fragrances, aluminum is useful since aluminum is relatively inert to fragrances. Aluminum can also be deep drawn into canisters and caps without cracking. Metal coated with polymers such as TEFLON or suitable plastic could also be used to increase the inertness.

The volatile fluid, vapor permeable membrane 13 is a key element of the invention. Through the membrane diffusion of the volatile substance occurs. This membrane controls the diffusion rate of volatile substance. Preferred membranes have porosity (e.g. microporosity), however some non-porous membranes may also be used. For permeable membranes, the diffusion rate will depend upon the membrane's porosity, pore size and membrane thickness. The diffusion membrane 13 may be made of a material chosen from various microporous polymers such as polypropylene, TEFLON, polyethylene, etc. Preferably, microporous TEFLON is used since it is an inert material for most volatile substances. The microporous membrane 13 is placed at the bottom of the closed end of the canister 11 as shown in FIGS. 1 and 2.

A grommet 12 may be made up of polymer such as nylon or TEFLON or polypropylene and the cap 16 may be made of the same material as the canister, since the cap too should be inert to the volatile substance.

FIG. 2 illustrates a process of assembling the button cell device from various components. A total of five components besides perfume and perfume absorbent materials are preferably used to construct the cell. These five components are sketched and illustrated in FIG. 2.

Two subassemblies were fabricated; the canister-membrane subassembly 18 and the cap-grommet subassembly 19 (FIG. 2). The cap-grommet subassembly 19 is filled with absorbent material such as glass wool, polymer wool, simple cotton fibers, or similar material. To this absorbent material, volatile substance 17 is then added to the absorbent material. Alternatively, gelled (e.g. by the addition of an appropriate thickener) volatile fluid is added in the cap-grommet subassembly (FIG. 2).

The volatile substance can be perfume, cologne, toilet water or other fragrance straight from the bottle, or can be a fragrant substance such as an oil (e.g. cinnamon or clove oil) admixed with an organic or other solvent (e.g. ethanol, water, isopropanol, methanol, etc.).

The canister-membrane subassembly 18 was then placed over grommet-cap subassembly 19 and then the whole button cell 10 was crimped in the crimping machine to form the final device as shown in FIG. 2. The assembly is preferably crimped to form seals between the membrane and perimeter of the canister as the canister and the cap. The device looks like a watch battery or calculator battery with holes at the bottom of the canister. Volatile substance releases through these apertures.

These holes are preferably sealed off with impermeable metallic or polymeric adhesive tape so that the volatile substance cannot escape during storage conditions. The tape also serves as a means to activate the device just when one wants to use it. Once the impermeable adhesive tape 15 is pulled away, the device starts emanating the vapor of volatile fluid through the microporous membrane 13 and canister apertures 4.

Although the preferred embodiment of the instant invention is a button cell device having a height to width ratio of less than 1, the cylindrical device can alternatively have a height to width ratio of greater than 1.

FIGS. 5 & 6 illustrate how a button cell perfume emanating device may be incorporated into an earring. The button cell micro device can be easily glued, clipped, or magnetically associated with a cavity of the earring. The button cell device also can be gold- or silver-plated for appearance sake. The advantage of magnetically holding the device is that one can easily exchange the button cell device for another with a different perfume. Alternatively the device may be placed in other jewelry such as earrings, locket, bracelet, or a tie-pin.

The invention provides a unique, very low cost device for the controlled release of volatile substances using standard or modified button cell battery components. The invention can provide a robust miniature device for incorporation into ornaments, jewelry, and therapeutic structures. The invention can also provide a rugged and low cost means of hermetically sealing between the microporous membrane and the volatile fluid-containing reservoir so that the volatilization of substance occurs through the microporous membrane at a controlled and linear rate.

Advantages for the design include: the fact that extremely small devices can be made (the canister can be as small as two (2) mm diameter by one (1) mm height); high-volume rugged hermetic seal production leads to a very inexpensive, yet reliable seal design enabling controlled uniform release through the microporous membrane; uniform thermal distribution in the fluid due to the thermally conductive metallic container leading to linear vaporization; and the use of a rugged material (metal) for the housing as well as proven seal design in contrast with a relatively delicate plastic housing with a relatively delicate membrane seal design.

These design advantages can lead to special applications for the invention, such as a "micro" device (typically 5 mm diameter×2 mm height) for perfume located in personal jewelry, an air fragrance vaporizer for delivery of room air freshener (optionally incorporated into a decorative outer shell), a medicament vaporizer useful for, for example, respiratory therapy (e.g. epinephrine or amyl nitrite), and a pest repellent or pesticidal device.

The invention is further explained by the following illustrative EXAMPLES:

EXAMPLE I

The device shown in FIG. 1 was fabricated. The metal canister with one (0.020 inches diameter) aperture was fabricated out of stainless steel, while the grommet was fabricated out of DuPont NYLON 101. The cap was fabricated out of copper-clad stainless steel. The diffusion microporous membrane was microporous PTFE (0.004 inches thick) obtained from W. L. Gore & Associates Inc. The membrane was 25% porous.

First, the microporous membrane was cut into a circular size of the internal diameter of the canister so that the membrane could fit snugly into the canister's bottom. In the first experiment, five layers of 0.004 inches thick membranes were used. Initially, two subassemblies were fabricated canister-membrane subassembly and cap-grommet subassembly. The cap-grommet subassembly was used as a small cup in which non-woven glass fiber obtained from Electrolock Inc. was filled. To this cup, 0.2 grams of volatile perfume/fragrance was added. Once the perfume/fragrance was all absorbed in the non-woven glass material of cap-grommet subassembly, then the canister-membrane subassembly was placed over the cap-grommet subassembly and the whole cell was crimped in a crimping machine. Non-porous TEFLON tape was cut to size, and placed over apertures of the cell for avoiding premature volatilization of the perfume In order to use the device, the adhesive tape was removed from the cell and the cell was weighed immediately. The cell was kept in an open plastic dish with the cell aperture open to the atmosphere. The weight loss due to volatilization of the perfume was measured and recorded. The temperature was ambient temperature (25° C.±5° C.). FIG. 3 shows the weight loss in grams vs time in days for this cell. The crimped cell had dimensions of 11.5 mm diameter by 5.5 mm height.

EXAMPLE II

Figure 4:
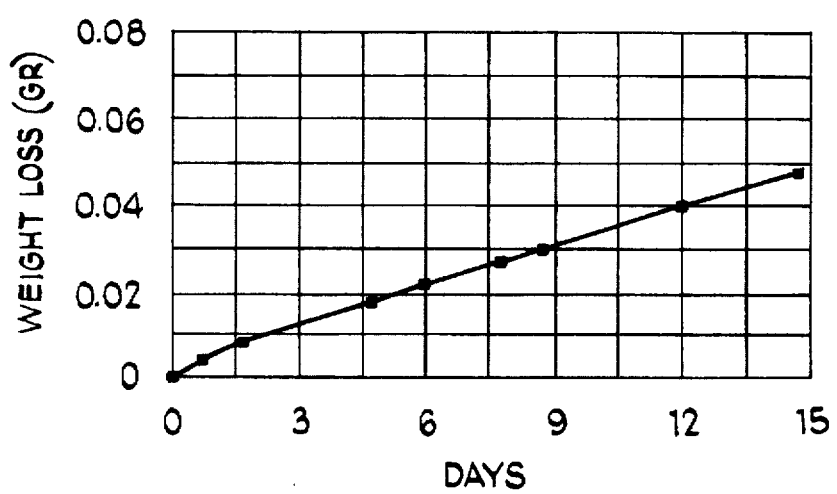
FIG. 4 is a graph depicting weight loss in mass (grams) versus time (days) from a fragrance-releasing button cell device of a size similar to that depicted in FIG. 2, except that eight layers of diffusion membranes are used instead of five layers.

A second experiment was carried out on another fabricated cell of the same dimensions (11.5 mm diameter by 5.5 mm height). The same procedure as in EXAMPLE I was followed, except that eight layers of microporous TEFLON membrane were used instead of the five layers of EXAMPLE I. The results of weight-loss of fragrance are shown in FIG. 4.

EXAMPLE III

The cell device as manufactured as in EXAMPLES I & II is incorporated into an earring as shown in FIGS. 5 & 6 with the aperture facing the atmosphere so that upon removal of adhesive sealant tape the volatile fragrance starts emanating from the device. A few drops of perfume will last for months.

Although the invention has been described with regard to certain preferred embodiments, the scope of the invention is to be defined by the appended claims.

What is claimed is:

1. A volatile substance releasing device comprising:

a housing comprised of a thin-walled substantially metal canister, said housing having a closed end with at least one aperture therein and a second, open end;

at least one layer of a permeable membrane positioned in the housing in abutting relationship against the closed end resulting in a canister permeable membrane subassembly, said permeable membrane permeable to fluidized volatile substance;

a cap having an open end and exterior walls and a grommet in abutting relationship with at least a portion of the exterior walls resulting in a grommet-cap subassembly having an open end and being sized and adapted to fit snugly within said housing and in contact with the periphery of said permeable membrane;

a composite comprising volatile fluid and absorbent, positioned in abutting relationship with said permeable membrane and the cap of the device and;

means for providing controlled rates of diffusion and linear vaporization of the volatile fluid through the permeable membrane comprising:

the canister permeable membrane subassembly operatively crimped over the open end of the grommet-cap subassembly so as to form a seal between the canister and the cap of the grommet-cap subassembly, as well as to form a seal between the canister and the permeable membrane along the perimeter of the closed end of the canister.

2. The volatile substance releasing device of claim 1 wherein the grommet-cap subassembly is of substantially the same height as the housing's wall.

3. The volatile substance releasing device of claim 1 further comprising tape placed on the aperture of the housing.

4. The volatile substance releasing device of claim 3 wherein the tape is made of a metallic or non-porous polymeric material or combinations thereof.

5. The volatile substance releasing device of claim 1 wherein the membrane consists of a controlled-porosity polymeric membrane inert with the volatile substance.

6. The volatile substance releasing device of claim 1 wherein the grommet-cap subassembly consists of a non-porous polymer grommet and metallic or plastic coated metallic cap fit snugly together.

7. The volatile substance releasing device of claim 1 wherein the absorbent is made from a material selected from glass wool, polymer wool, non-woven polymer, cottonbased absorbent materials, and mixtures thereof.

8. The volatile substance releasing device of claim 1 wherein said volatile fluid includes a gelling agent.

9. The volatile substance releasing device of claim 1 wherein the housing is made of metal coated with plastic.

10. The volatile substance releasing device of claim 1 wherein the volatile fluid is a perfume.

11. The volatile substance releasing device of claim 1 wherein the volatile fluid is pesticide.

12. The volatile substance releasing device of claim 1 wherein the volatile fluid is an insect repellent.

13. The volatile substance releasing device of claim 1 wherein the volatile fluid is air fragrance.

14. The volatile substance releasing device of claim 1 wherein the volatile fluid is a medicinal fluid.

15. The volatile substance releasing device of claim 1 wherein the cap is made of a magnetic material.

16. The volatile substance releasing device of claim 1 comprising an item of jewelry.

* * * * *